US005696292A

United States Patent [19]
Cody et al.

[11] Patent Number: 5,696,292
[45] Date of Patent: Dec. 9, 1997

[54] PROCESS FOR PRODUCING QUARTERNARY AMMONIUM COMPOUNDS

[75] Inventors: Charles Cody, Robbinsville, N.J.; N. Ben Martin, Collierville, Tenn.

[73] Assignees: Witco Corporation, Greenwich, Conn.; Rheox, Inc., Highstown, N.J.

[21] Appl. No.: 388,059

[22] Filed: Feb. 10, 1995

[51] Int. Cl.$^6$ .................................................. C07C 209/12
[52] U.S. Cl. ............................ 564/296; 564/282; 564/288
[58] Field of Search ................................ 564/282, 288, 564/296

[56] References Cited

U.S. PATENT DOCUMENTS

| | | | |
|---|---|---|---|
| 4,069,347 | 1/1978 | McCarthy et al. | 424/358 |
| 4,096,072 | 6/1978 | Brock et al. | 252/8.8 |
| 4,184,970 | 1/1980 | Draper | 252/8.8 |
| 4,412,018 | 10/1983 | Finlayson et al. | 523/508 |
| 4,434,076 | 2/1984 | Mardis et al. | 252/315.2 |
| 4,450,095 | 5/1984 | Finlayson | 252/315.2 |
| 4,769,078 | 9/1988 | Tso | 106/287.25 |
| 4,795,573 | 1/1989 | Tsumadori | 252/8.8 |
| 4,834,048 | 5/1989 | House et al. | 501/148 |
| 4,857,310 | 8/1989 | Baydar | 424/70 |
| 4,876,030 | 10/1989 | Dixon et al. | 252/315.2 |
| 4,894,182 | 1/1990 | Cody et al. | 252/315.2 |
| 5,279,767 | 1/1994 | Phan et al. | 252/357 |
| 5,334,241 | 8/1994 | Jordan | 106/487 |
| 5,336,372 | 8/1994 | Cody et al. | 162/5 |
| 5,336,647 | 8/1994 | Nae et al. | 501/146 |
| 5,391,368 | 2/1995 | Gerstein | 424/70.13 |
| 5,409,640 | 4/1995 | Giret et al. | 252/546 |
| 5,414,124 | 5/1995 | Smith et al. | 564/282 |
| 5,417,868 | 5/1995 | Turner | 252/8.8 |
| 5,443,631 | 8/1995 | Brock et al | 106/244 |
| 5,482,636 | 1/1996 | Brock et al. | 252/8.8 |

FOREIGN PATENT DOCUMENTS

| | | |
|---|---|---|
| 0 004 108 | 9/1979 | European Pat. Off. |
| 0 008 839 | 3/1980 | European Pat. Off. |
| 0122 140 | 10/1984 | European Pat. Off. |
| 0 440 229 | 8/1991 | European Pat. Off. |
| 0 604 726 | 7/1994 | European Pat. Off. |
| 58-067649 | 10/1981 | Japan . |
| 61-275398 | 12/1986 | Japan . |
| 1 602 187 | 11/1981 | United Kingdom . |

*Primary Examiner*—Peter O'Sullivan
*Attorney, Agent, or Firm*—Evenson, McKeown, Edwards & Lenahan, P.L.L.C.

[57] ABSTRACT

Process for the preparation of quaternary ammonium compounds, by preparing a mixture of a tertiary amine and a liquid reaction vehicle and adding an alkyl halide to the mixture to produce a quaternary ammonium halide, the liquid reaction medium being a liquid, low volatility, substantially non-toxic diluent having a vapor pressure not greater than about 1 mm. Hg at a temperature of 25° C. and preferably being a fatty acid or a fatty acid mono-, di-, or triglyceride, a mineral oil, or 2-ethylhexanol wherein the alkyl groups comprising the fatty acids or the triglycerides have from about 10 to about 24 carbon atoms, the quaternary ammonium compounds being particularly suited for uses such as deinking of paper in conjunction with appropriate clays, surfactants, flotation agents, anti-static agents and biocides.

40 Claims, 1 Drawing Sheet

QUATERNARY AMMONIUM CHLORIDE MANUFACTURING PROCESS

PROCESS FOR PRODUCING QUARTERNARY AMMONIUM COMPOUNDS

BACKGROUND OF THE INVENTION

The present invention relates to novel methods of preparing quaternary ammonium compounds in good yields, and more particularly, it relates to processes for the preparation of certain long-chain quaternary ammonium compounds with novel diluents which obviate disposal and environmental problems associated with their preparation and usage.

Novel compositions of the long-chain quaternary ammonium compounds and diluent and methods for their use are the subject of a separate patent application entitled "Novel Quaternary Ammonium Compositions and Their Uses" which is being filed simultaneously herewith in the name of Charles Cody et al. and is incorporated herein by reference in its entirety.

Quaternary ammonium compounds (sometimes abbreviated as "quats") of the type useful in this invention are salts of organic cations which have a positive charge localized on a nitrogen atom and a charge neutralizing anion designated X.

Quaternary ammonium compounds have the following formula:

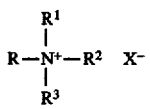

These quaternary ammonium compounds may be described as having four moieties where R is an organic radical and $R^1$, $R^2$ and $R^3$ are organic radicals or hydrogen. The groups attached to the central nitrogen atom are typically selected from the group consisting of (a) alkyl groups; (b) aralkyl groups which are benzyl and substituted benzyl moieties; (c) aryl groups such as phenyl; (d) beta, gamma-unsaturated groups having six or fewer carbon atoms, (e) hydroxyalkyl groups having 2 to 6 carbon atoms; and (f) hydrogen. The principal groups above are most often derived from naturally occurring fats or oils such as tallow, corn oil, soybean oil, cottonseed oil, castor oil, linseed oil, safflower oil, palm oil, peanut oil and the like. Mixtures of oils are commonly employed. The oil may be of natural sources, or a synthetic version of same, or modifications of a naturally occurring oil using known techniques. A broad listing of the useful components used to make quaternary ammonium compounds ("quats") is described in U.S. Pat. No. 5,336,647.

$X^-$ is an anion which usually is chloride, methyl sulfate, bromide, iodide, hydroxyl, nitrite or acetate. The anion accompanying the organic cation is selected so as not to affect adversely the intended use of the quaternary ammonium compound, and may optionally be selected to impart unique characteristics to the quaternary compound.

Commercially significant quats usually contain at least one residue of a naturally occurring oil, most often derived from beef tallow. In addition to the uses previously mentioned, these quaternary ammonium compounds also find utility as surfactants, anti- static agents, flotation agents, biocides, and, as stated, as reactants in the formation of organically-modified clay rheological control additives for paints, coatings, drilling muds and the like. In addition, poly-quaternary compounds with more than one nitrogen atom have been utilized and are included in the definition of quaternary ammonium compounds.

Numerous methods are known for the preparation of quaternary ammonium compounds. The method chosen will depend upon the particular groups substituent on the nitrogen atom and the end uses to which the products of the reaction will be put. In general, the most convenient reactions involve a suitable amine and an alkylating agent. Commercially, the amines are obtained from natural or synthetic sources.

Generally, the manufacture and preparation of quaternary ammonium compounds or salts is achieved by techniques well-known in the art. When preparing a quaternary ammonium compound, one skilled in the art can prepare a dialkyl secondary amine, for example, by the hydrogenation of nitriles, and then form the methyl dialkyl tertiary amine by reductive alkylations using formaldehyde or dimethoxymethane as a source of the methyl radical. A commercial manufacturing process typically involves various stages, including those resulting in the creation of nitriles, primary amines, secondary and tertiary amines, and finally the quaternary compound itself.

The manufacturing process may involve saturation of fatty acids derived from tallow, or of a commercial natural oil, by hydrogenation as an early step. The products are sometimes called "hydrogenated tallow", or "HT", when describing common quaternary ammonium compounds, even those not exclusively derived from tallow fatty acids. Saturated, relatively long-chain hydrocarbon molecules are typically solids or very highly viscous liquids at room temperatures. The quaternization step is done in a liquid medium in order to solvate and reduce the viscosity of the both the starting material and the reaction products, and to reduce foaming. The medium used for commercial processing has almost universally been lower alkyl alcohols, most prominently isopropyl alcohol (IPA).

Quaternization reactions are typically carried out in the presence of an inorganic alkali—such as sodium bicarbonate, sodium hydroxide, sodium or calcium carbonate—to react with any acid that may be formed as a by-product from the reaction of the alkylating agent (typically an alkyl or aralkyl halide) with labile hydrogen compounds contained within the reaction mixture. Such acidic materials form salts with the amine reactant, deactivating it toward quaternization. Such labile hydrogen compounds include, but are not limited to, primary and secondary amines—typically from incomplete reductive alkylation of the amine in the preceding step—and also water.

A variety of methods for producing quaternary compounds is mentioned in the article "Quaternary Ammonium Compounds" commencing at page 521 in Volume 19 of the Encyclopedia of Chemical Technology. Shapiro et al U.S. Pat. No. 2,775,617 describes preparation of tetraalkyl ammonium halides by the alkylation of alkyl secondary amines with alkyl halides, and states that the presence of hydrohalic acids is undesirable, so that strong bases are used to react with the acids. The reaction is carried out in the presence of water. Shapiro U.S. Pat. No. 2,950,318 shows reacting an alkyl halide and a primary or secondary amine with the introduction of sodium hydroxide to prepare quaternary ammonium chloride. The reactor is initially charged with primary or secondary amine and a low-boiling alcohol, preferably isopropanol.

Shapiro et al U.S. Pat. No. 3,175,008 shows the preparation of quaternary ammonium compounds by reacting secondary amines with an alkyl halide in the presence of sodium bicarbonate and with the addition of caustic. Again, a low boiling alcohol is used as a solvent. Gysin et al U.S. Pat. No. 2,644,003 shows the preparation of quaternary ammonium compounds utilizing acetanilide compounds in ethyl acetate or benzene. Baydar U.S. Pat. No. 4,857,310 shows triglyceride quaternary ammonium compounds and their preparation, for instance, by reacting castor oil with chloroacetyl chloride. This reference shows the use of toluene, chloroform, or dichloromethane as solvents at one stage and ethanol in another stage. In some instances, quaternary ammonium compounds have also been prepared in propylene glycol or hexylene glycol.

While prior art methods for the production of quaternary ammonium compounds by the reaction of secondary amines and alkyl halides successfully produce quaternary ammonium product, the use of low-boiling alcohols in the process has created difficulties. One reason for the use of such alcohols is to provide a fluid, low-viscosity volatile reaction medium. As noted in the prior art, isopropanol is a preferred solvent.

After manufacture, unless the product specifications call for powdered product (which requires expensive vacuum distillation and spraying or even grinding) the commercial quaternary ammonium compounds are sold in solution. In certain applications the solution is an isopropanol solution, referred to in the aforementioned copending application as a "quaternary ammonium composition". In general, customers have no commercial use for the isopropanol following the reaction or blending of the quaternary ammonium material in their end uses. Thus, the isopropanol is frequently discharged indirectly into a publicly owned treatment works or into some private disposal system, in which latter case significant expense is incurred for destruction and/or disposal of toxic isopropanol. As environmental controls on indirect discharges into publicly owned treatment works are increased, the cost of the isopropanol disposal is rising. For reasons of environmental protection and cost, it would be desirable to have a process for the preparation of quaternary ammonium compounds, which process would be more environmentally acceptable, both in production and use. Other advantages can also result from use of alternative processes.

The media described in the prior art, in the main, involve mostly volatile organic compositions which share a number of properties, the most important of which is the low temperature at which they exhibit a vapor pressure of approximately 1 mm. For example ethanol exhibits a vapor pressure of 1 mm, at a temperature of −31° C. while toluene's temperature is −26.7° C. and methanol's is −44° C. While glycols exhibits a vapor pressure of 1 mm at higher temperatures, they present problems of toxicity, odor, flammability and solubility in water systems where the quaternary may be used, that they have not been widely used. Most of the solvents employed in the conventional manufacture of quaternary ammonium compounds can be further characterized as having toxicity, low viscosity, low flash and freezing points. In particular, the vapor pressure of almost all the prior art vehicles substantially exceeds 1 mm of Hg at 25° C.

SUMMARY OF THE INVENTION

Briefly, the present invention alleviates the problems encountered in prior art processes for the production of quaternary ammonium compounds by reacting suitable alkyl or arylalkyl tertiary amines with an alkyl halide in the presence of a liquid, low volatility, substantially non-toxic diluent having a vapor pressure not greater than about 1 mm Hg at a temperature of 25° C. and are liquids at the reaction temperature used to carry out the quaternization. As disclosed further herein, such a reaction provides quaternary ammonium compounds in good yields and with environmentally sound technology.

Desirable diluents for use in practicing the process are particularly exemplified by non-volatile, non-toxic compositions such as long-chain fatty acids, long-chain fatty acid mono-, di-, and triglycerides, mineral or naphthenic oils, or 2-ethylhexanol diluents. These diluents not only provide good reaction rates with relatively low pressures being used and good safety for the process and the environment, but they also provide numerous other advantages, including products which can be directly utilized in a wide variety of industrial processes.

The use of conventional solvents for the preparation of quaternary compounds results in the presence of alcohols, as well as water, which are thought to act as "protonizing" agents in the process. It has, however, been found according to the present invention that the selected diluents as taught herein result in good yields of, and good reaction completeness to form, the desired quaternary ammonium compounds.

Use of the novel diluents according to the present invention also permits the use of higher temperatures for a given pressure, which can in turn result in greater reaction completion and a higher yield of desirable product. The diluents of the present process can be stored and transported safely. Their viscosities under the reaction conditions provide for easy and thorough mixing of the reactants in the diluents.

The process according to the present invention provides quaternary ammonium composition which not only obviate the need to handle and dispose of alcohols such as isopropanol, but it has been found that use of diluents of the invention confers further advantages. The diluents have low evaporation rates which make them useful in a variety of products. Further, they have high flash points (that is, they are relatively non-flammable) and many of them can readily be obtained in a form which is liquid at room temperatures. The economy of the quaternary-producing reaction is also enhanced by virtue of little or no loss of diluent, either during processing or in the finished material.

Further, as an additional benefit, the diluents used in the present processes provide quaternary ammonium chlorides with improved performance in a number of end uses. For instance, the quaternary ammonium compositions produced according to the present invention give improved results in the use of organoclays and in surface active compositions. Moreover, their qualities suit them for use in new applications in soap and cosmetic manufacture and particularly for use in deinking processes for waste paper treatment and recycling, all as described in greater detail in my aforementioned copending application.

BRIEF DESCRIPTION OF THE DRAWING

The invention is further described with reference to the accompanying drawing, wherein.

DETAILED DESCRIPTION OF THE PREFERRED EMBODIMENTS

Figure 1:
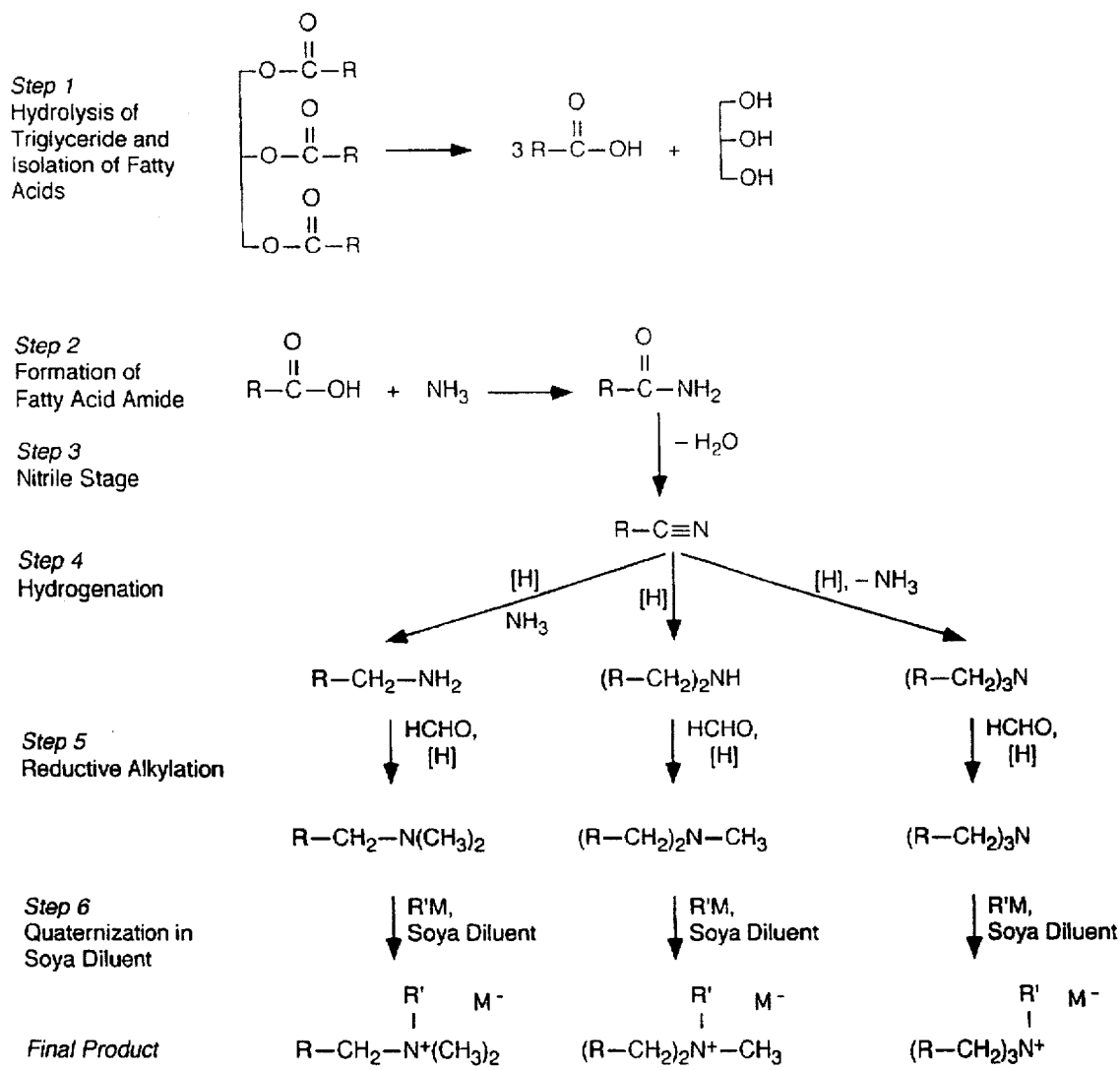
FIG. 1 is a flow diagram illustrative of a preferred process for manufacturing quaternary ammonium halides according to the present invention.

Referring first to the drawing, in Step 1, the starting material, a fatty acid triglyceride, is hydrolyzed and the fatty acids are recovered. The fatty acids so obtained are reacted in Step 2 with ammonia to form a nitrile. The fatty acid alkyl radicals, if desired, can be partially or completely hydrogenated either before or after the hydrolysis.

In Step 3, the nitrile so obtained is converted to an amine by catalytic hydrogenation. Depending on the reaction conditions employed, the principal product of this catalytic hydrogenation is either a primary, secondary or tertiary amine. For instance, if the hydrogenation is carried out at high ammonia pressure, the principal product is a primary amine; alternatively, if the hydrogenation is carried out in the absence of added ammonia partial pressure, the principal product is a secondary amine. Usually the amine product is then subjected to reductive alkylation using formaldehyde or a formaldehyde equivalent to form a tertiary amine; the product of this reductive alkylation of a primary amine is a dimethyl alkyl amine and, of a secondary amine, a methyl dialkyl amine. Although tertiary amines will not undergo reductive alkylation, the products of the catalytic hydrogenation of nitriles to form them are usually subjected to reductive alkylation conditions to convert any primary and secondary amine impurities to tertiary amines.

These tertiary amines are then diluted with at least one diluent according to the present invention at Step 4, before the source of chloride ions is then added in Step 5. Step 6 is the quaternization step in the presence of the diluents of the present invention. In Step 7, the final quaternary ammonium composition results.

The tertiary amine starting materials for the present process can be selected from a variety of alkyl tertiary amines or arylalkyl tertiary amines. It is generally preferred that at least one alkyl group be a long-chain alkyl having from about six to about 24 carbon atoms in the chain. The chain can be saturated or it can be mono- or polyunsaturated. The other two chains can be lower alkyl containing from one to four carbon atoms or one of the substituents can be aryl. The second and third moieties can be independently selected from groups comprising short chain (e.g., one to four carbon atoms) alkyl, long chain (e.g., eight to 24 carbon atoms) alkyl, aralkyl wherein the alkyl portion of the moiety contains one to 22 carbon atoms, hydroxyalkyls and polyhydroxyalkyls.

In certain embodiments of this invention, one substituent is preferably a linear or branched, saturated or unsaturated alkyl group having 12 to 22 carbon atoms. The remaining groups of the cation can be selected from the group consisting of (a) linear or branched aliphatic, alicyclic or aromatic groups having one to 22 carbon atoms; (b) aralkyl groups which are benzyl and substituted benzyl moieties including fused ring moieties having linear chains or branches of one to 22 carbon atoms in the alkyl portion of the structure; (c) aryl groups such as phenyl and substituted phenyl including fused ring aromatic substituents; (d) β, γ-unsaturated groups having six or less carbon atoms or hydroxyalkyl groups having two to six carbon atoms; and (e) hydrogen.

The long chain alkyl radicals may be derived from naturally occurring oils including various vegetable oils, such as corn oil, coconut oil, palm oil, palm kernel oil, soybean oil, cottonseed oil, rapeseed or canola oil, olive oil, peanut oil, safflower seed oil, castor oil and the like, as well as various animal fats such as tallow. The alkyl radicals may likewise be petrochemically derived from, for example, alpha olefins.

Representative examples of useful branched, saturated radicals include 12-methylstearyl and 12-ethylstearyl. Representative examples of useful branched unsaturated radicals include 12-methyloleyl and 12-ethyloleyl. Representative examples of unbranched, saturated radicals include lauryl; stearyl; tridecylmyristyl(tetradecyl); pentadecyl; hexadecyl; and hydrogenated tallow, docosanyl. Representative examples of unbranched, unsaturated and unsubstituted radicals include oleyl, linoleyl, linolenyl, soya and tallow.

Additional examples of aralkyl, that is benzyl and substituted benzyl moieties, include those materials derived from, e.g., benzyl halides, benzhydryl halides, trityl halides, α-halo-α-phenylalkanes wherein the alkyl chain has from one to 22 carbon atoms, such as 1-halo-1-phenylethane, 1-halo-1-phenyl propane, and 1-halo-1-phenyloctadecane; substituted benzyl moieties, such as those derived from ortho-, meta- and para-chlorobenzyl halides, para-methoxybenzyl halides, ortho-, meta- and para-nitrilobenzyl halides, and ortho-, meta- and para-alkylbenzyl halides wherein the alkyl chain contains from one to 22 carbon atoms; and fused ring benzyl-type moieties, such as those derived from 2-halomethylnaphthalene, 9-halomethylanthracene and 9-halomethylphenanthrene, wherein the halo group comprises chloro, bromo, iodo, or any other such group which serves as a leaving group in the nucleophilic attack of the benzyl type moiety such that the nucleophile replaces the leaving group on the benzyl type moiety.

Examples of aryl groups that are useful as the first organic substituent include phenyl and substituted phenyl, N-alkyl and N,N-dialkyl anilines, wherein the alkyl groups contain between one and 22 carbon atoms; ortho-, meta- and para-nitrophenyl, ortho-, meta- and para-alkyl phenyl, wherein the alkyl group contains between one and 22 carbon atoms, 2-, 3-, and 4-halo-phenyl wherein the halo group is defined as chloro, bromo, or iodo, and 2-, 3-, and 4-carboxyphenyl and esters thereof, where the alcohol of the ester is derived from an alkyl alcohol, wherein the alkyl group contains between one and 22 carbon atoms, aryl such as a phenol, or aralkyl such as benzyl alcohols; fused ring aryl moieties such as naphthalene, anthracene, and phenanthrene.

The β, γ-unsaturated alkyl group which can be included in the first organic component can be selected from a wide range of materials well known in the art. These compounds may be cyclic or acyclic, unsubstituted or substituted with aliphatic radicals containing up to three carbon atoms such that the total number of aliphatic carbons on the β, γ-unsaturated radical is six or less. The β, γ-unsaturated alkyl radical may be substituted with an aromatic ring that likewise is conjugated with the unsaturation of the β, γ moiety or the β,γ radical may be substituted with both aliphatic radicals and aromatic rings.

Representative examples of cyclic β, γ-unsaturated alkyl groups include 2-cyclohexenyl and 2-cyclopentenyl. Representative examples of acyclic γ, β-unsaturated alkyl groups containing six or less carbon atoms include propargyl; allyl(2-propenyl); crotyl(2-butenyl); 2-pentenyl; 2-hexenyl; 3-methyl-2-butenyl; 3-methyl-2-pentenyl; 2,3-dimethyl-2-butenyl; 1,1-dimethyl-2-propenyl; 1,2-dimethyl propenyl; 2,4-pentadienyl; and 2,4-hexadienyl. Representative examples of acyclic-aromatic substituted compounds include cinnamyl(3-phenyl-2-propenyl); 2-phenyl-2-propenyl; and 3-(4-methoxyphenyl)-2-propenyl. Representative examples of aromatic and aliphatic substituted materials include 3-phenyl-2-cyclohexenyl; 3-phenyl-2-cyclopentenyl; 1,1-dimethyl-3-phenylpropenyl; 1,1,2-trimethyl-3-phenyl-2-propenyl; 2,3-dimethyl-3-phenyl-2-propenyl; 3,3-dimethyl-2-phenyl-2-propenyl; and 3-phenyl-2-butenyl.

The hydroxyalkyl group can be selected from a hydroxyl substituted aliphatic radical wherein the hydroxyl is not substituted at the carbon atom adjacent to the positively charged atom; the group has from two to six aliphatic carbon atoms. The alkyl group may be substituted with an aromatic ring independent of the two to six aliphatic carbons. Representative examples include 2-hydroxyethyl; 3-hydroxypropyl; 4-hydroxypentyl; 6-hydroxyhexyl; 2-hydroxypropyl; 2-hydroxybutyl; 2-hydroxypentyl; 2-hydroxyhexyl; 2-hydroxycyclohexyl;

3-hydroxycyclohexyl; 4-hydroxycyclohexyl; 2-hydroxycyclopentyl; 3-hydroxycyclopentyl; 2-methyl-2-hydroxypropyl; 1,1,2-trimethyl-2-hydroxypropyl; 2-phenyl-2-hydroxyethyl; 3-methyl-2-hydroxybutyl; and 5-hydroxy-2-pentenyl.

The anion in the quaternary compounds produced according to the invention is typically one that will not adversely affect the reaction product or the recovery of the same. Such anions include, for example, chloride, bromide, iodide, and methyl sulfate used in amounts sufficient to neutralize the organic cation.

The preparation of the amine can be achieved by techniques well-known in the art. For example, when preparing a quaternary ammonium salt, one skilled in the art would prepare a dialkyl secondary amine, for example, by the hydrogenation of nitriles, see U.S. Pat. No. 2,355,356, and then form the methyl dialkyl tertiary amine by reductive alkylation using formaldehyde as a source of the methyl radical. According to procedures set forth in U.S. Pat. No. 3,136,819 and U.S. Pat. No. 2,775,617, a quaternary amine halide can then be formed by adding benzyl chloride or benzyl bromide to the tertiary amine. The disclosures of the above three patents are incorporated herein by reference.

The alkylating agents used herein are lower alkyl halides. The alkyl group can contain from one to four carbon atoms. In certain embodiments it is desirable to use a methyl halide. Generally, the halide is chloride, bromide, or iodide, with the chloride being preferred in commercial embodiments.

In certain especially preferred embodiments, the quaternary ammonium chlorides produced according to the present invention can have two long-chain alkyl groups derived from hydrogenated tallow, with the alkyl group being methyl, or a long-chain alkyl and an aromatic group such as benzyl. Such especially preferred quaternary ammonium halides include dimethyldi(hydrogenated tallow) ammonium chloride ("2M2HT"), benzyldimethyl(hydrogenated tallow) ammonium chloride, and benzylmethyldi(hydrogenated tallow) ammonium chloride.

The reaction to provide the quaternary ammonium compounds according to the present invention can be carried out over a range of temperatures. Too low a temperature will result in a very low reaction rate, and in extreme cases, some of the reactants may lose their liquidity. Too high a temperature can cause thermal degradation of the reactants and products, can create thermal hazards, and can cause unwanted side reactions to occur. It is accordingly desirable to carry out the reaction at a temperature which will permit all of the reactants to be liquid and which will provide good yields of the desired quaternary ammonium compounds.

It has generally been found according to this invention that the reaction temperature can be from about 50° to about 220° F. (about 10° to about 104° C.). In certain preferred embodiments, it is desirable for the reaction to be carried out at from 190° to 220° F. (about 87.7° to about 104° C.), and in certain preferred embodiments, temperatures of 180° to 200° F. (about 82° to about 93° C.) are used.

Generally, the reaction is carried out for from about two hours to 24 hours, more particularly, from about 2 hours to about 12 hours. If desired, the alkyl or aryl halide can be added in part, with the remainder being added when the reaction is proceeding. The use of degummed triglycerides as diluents, such as degummed soybean oil, can reduce or eliminate the need for antifoaming agents.

In certain embodiments of the process of this invention, it is desirable to carry out the quaternization in the presence of an alkaline material. Such materials react with any acidic materials which may be formed during the reaction, as a by-product of the reaction of the alkylating agent, such as methyl chloride, and with any labile hydrogen compounds which may be present in the reaction mixture. Inorganic alkalis such as alkali metal or alkaline earth metal carbonates, bicarbonates, and/or hydroxides can be used in such embodiments. Sodium bicarbonate, sodium carbonate, sodium hydroxide, and calcium carbonate are used in certain preferred embodiments, with sodium hydroxide being especially preferred.

The diluents employed in this invention can be described as having a vapor pressure of 1 mm or less at a temperature of 25° C. and are liquids at the reaction temperature. Mono-, di-, and triglycerides; fatty acids; mineral or naphthenic oils; and 2-ethylhexanol can be used, as taught herein, and it is especially desirable to use triglycerides of fatty acids. These fatty acids and glycerides have alkyl groups generally containing from 10 to 24 carbon atoms. The alkyl chains can be fully saturated or mono-, di-, or poly-unsaturated, depending upon the processing conditions and the properties desired in the final quaternary ammonium compound. While the natural materials frequently contain an even number of carbon atoms, triglycerides with alkyl chains having either an odd or even number of carbon atoms can be used.

The particular diluents selected can also depend upon the foaming properties thereof. Foaming is undesirable since, among other things, it fills void space in the reaction vessel and interferes with the addition of the alkyl halide and the reaction completion. In certain desirable embodiments, degummed triglycerides are accordingly used. One very useful diluent is degummed, refined, bleached soybean oil, as it has a reduced tendency to foam during the course of the reaction.

Since a broad range of triglycerides and other diluents can be used, it is a feature of the present process in certain preferred aspects to utilize an antifoaming agent such as silicone-containing compounds. In certain preferred embodiments, dimethyl polysiloxanes can be used. Dow Corning 1400 and 1410 antifoam emulsions have been found to be particularly well-suited to carrying out the present invention.

The acid, glyceride, mineral, and alkylhexanol diluents are as described herein. The mineral oils are also generally described as petrolatum oils or liquid paraffins. Typically, they are colorless to slightly colored and are relatively tasteless and odorless. They are a mixture of liquid hydrocarbons from petroleum. In certain embodiments of the present invention, the fatty acids and particularly the triglycerides are used as diluents.

The quantity of diluent is such that the compositions are liquid or can be made liquid at temperatures slightly above room temperature, with sufficient quaternary compound to have the desired activity in the selected use. Typically, the amount of diluent in the compositions can be from about 10 to about 90 percent of the weight of the total composition. In certain preferred embodiments, it is desired that the quantity of diluent range from about 20 to about 60 percent of the weight of the total composition. It will be appreciated from the present disclosure that the compositions can also contain minor amounts of other materials used in the process for their preparation, such as antifoaming agents and the like, as well as materials which can suit them for particular uses for which they are uniquely suited. Briefly, such uses include the preparation of organoclays for waste paper or pulp deinking, use in cosmetics, in fabric softener compositions, and the like.

It has been found that the quaternary ammonium halides produced according to the present invention are quite well suited to a variety of uses. Thus, they are especially adapted in one embodiment to use in deinking processes, such as those described in Cody et al U.S. Pat. No. 5,151,155 because they readily react with the smectite clays. The diluent vehicles of the present invention do not interfere with this use, are less toxic, have a higher flash point (so that it is considered non-flammable), and do not create disposal problems.

The quaternary ammonium compounds provided according to the present process are also well suited to use for other known products. Thus, they can be used in viscosity-increasing additives for non-aqueous systems. Such uses are illustrated in Finlayson U.S. Pat. No. 4,208,218.

The following Examples are given to illustrate embodiments of the invention as it is presently preferred to practice it. It will be understood that these Examples are illustrative, and the invention is not to be considered as restricted thereto and is only limited by the appended claims.

All parts, percentages, proportions, and ratios herein are by weight, unless otherwise indicated.

EXAMPLE I

A reaction vessel was charged with 240 lb. (about 108.864 kg.) of hydrogenated tallow derived monomethyl tertiary amine, together with 60 lb. (about 27.216 kg.) (20% of the weight of the amine) of degummed, bleached and refined soybean oil and 3.6 lb. (about 1,632.96 g.) (1.2%) of 50% aqueous caustic solution. Then, 0.21 lb. (about 95.256 g.) of Dow Corning 1400 silicone antifoam was added to the reaction mixture. Thereafter, 21 lb. (about 9.526 kg.) of methyl chloride was added over time, being 90% of the calculated stoichiometric amount.

The contents of the reactor were then heated to 205°–210° F. (about 96° –about 98.9° C.). This temperature was maintained for about 8.5 hrs, during which time the reaction mixture was sampled for color, total amine acid value, acid value, and pH. The reactor was held at temperature until the free amine and amine HCl were within the desired specification with the free amine being greater than the amine hydrochloride and the total being less than about 8.0%. The pH slowly fell from about 7.8 to 7.0.

It was found that the reaction was not complete, so the reactor was then cooled to about 140° F., and an additional amount of methyl chloride (2.0 lbs. (about 907.2 g.)) was added to the vessel. The reactor contents were again heated to about 200°–210° F. (about 93.3°–about 98.9° C.) and held for another nine hours at that temperature. During this time, the pH fell from about 6.6 to about 6.2. Thereafter, the reactor contents were cooled to 190° F. (about 87.8° C.) and filtered. No foaming was encountered during the filtration.

The 264 lb. (about 119.750 kg.) of dimethyldi (hydrogenated tallow) ammonium chloride in diluent so produced had a color of 8+, total amine value of 4.2, amine number of 3.1, and a pH of 5.8.

EXAMPLE II

A reaction vessel was charged with 12.5 lb. (about 5.67 kg.) of stearic acid and 12.5 lb. (about 5.67 kg.) of hard (hydrogenated) tallow-derived monomethyl tertiary amine. The vessel was brought to 130° F. (about 54° C.), and 1.0 lb. (453.6 g.) of methyl chloride, 90% of the theoretical amount, was added.

The contents of the reactor were then heated to 200° F. (about 93° C.). After about one hour the temperature increased to 210° F. (about 98.9° C.). Samples were taken and when the free amine and amine HCl were within the desired specification, the contents were removed from the vessel. About 25 lb. (about 11.34 kg.) of dimethyldi (hydrogenated tallow) ammonium chloride was obtained with a pH of 4.2, a total amine value of 2.9 and an amine number of 2.0.

EXAMPLE III

A reaction vessel was charged with 27 lb. (about 12.247 kg.) of hard tallow derived monomethyl tertiary amine, 4.0 lb. (about 1.814 kg.) of refined soybean oil, 2.7 lb. (about 1.225 kg.) of 2-ethylhexanol, and 0.32 lb. (about 145.2 g.) of 50% aqueous caustic soda. The vessel was brought to 125° F. (about 51.7° C.), and 2.6 lb. (about 1.179 kg.) of methyl chloride, 90% of the theoretical amount, was added.

The contents of the reactor were then heated to 210° F. (about 98.9° C.). After about two hours the temperature decreased to 207° F. (about 97.2° C.). Samples were taken and when the free amine and amine HCl were within the desired specification, the contents were removed from the vessel. About 29 lb. (about 13.154 kg.) of dimethyldi (hydrogenated tallow) ammonium chloride product was recovered, with a Gardner color of 5+, an acid number of 2.4, a total amine value of 5.2, and a pH of 6.4.

EXAMPLE IV

A reaction vessel was charged with 500 g. of hard tallow derived monomethyl tertiary amine, 500 g. of paraffinic naphthenic diluent, 108 g. of methyl chloride, and 8 g. of sodium bicarbonate. The contents were reacted for five hours at 90° F. (about 32.2° C.) and 100 psig.

The recovered dimethyldi(hydrogenated tallow) ammonium chloride had a Gardner color less than one, a free amine of 1.7, an amine hydrochloride of 0.22, and a pH of 8.2.

EXAMPLE V

A reaction vessel was charged with 650 g. of hard tallow derived monomethyl tertiary amine, 350 g. of stearic acid, and 142 g. of methyl chloride. The contents were reacted for three hours at 90° F. (about 32.2° C.) and 100 psig.

The recovered dimethyldi(hydrogenated tallow) ammonium chloride had a Gardner color of 5, a total amine value of nil, an acid number of 6, and a pH of 2.6.

EXAMPLE VI

A reaction vessel was charged with 500 g. of hard tallow derived monomethyl tertiary amine, 500 g. of soybean oil, 108 g. of methyl chloride, and 6 g. of sodium bicarbonate. The contents were reacted for seven hours at 90° F. (about 32.2° C.) and 100 psig.

The recovered dimethyldi(hydrogenated tallow) ammonium chloride had a Gardner color of 11, a free amine of 3.9, an amine hydrochloride of 1.4, a pH of 5.4, and a melting point of 63.5° C.

It will be understood from the present invention by those skilled in the art that the use of various amines and alkylating agents will provide a variety of desirable lower alkyl and di- or tri-lower alkyl quaternary ammonium halides.

What is claimed is:

1. In a process for the preparation of quaternary ammonium halide compound which comprises preparing a mixture consisting essentially of an amine, a diluent, and an alkyl halide alkylating agent to produce a quaternary ammonium halide compound, and thereafter recovering said quaternary ammonium halide compound, the improvement comprising the diluent being selected from the group consisting of fatty acid triglycerides and 2-ethylhexanol.

2. The improvement of claim 1, wherein the alkyl groups comprising the triglyceride have from about 10 to about 24 carbon atoms.

3. The improvement of claim 1, wherein the amine is a tertiary amine having the formula

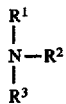

wherein $R^1$ is lower alkyl; $R^2$ is lower alkyl, long-chain alkyl, or aryl; and $R^3$ is long-chain alkyl.

4. The improvement of claim 3, wherein the lower alkyl contains from 1 to 4 carbon atoms, the long-chain alkyl contains from 10 to 24 carbon atoms, and the aryl is mononuclear.

5. The improvement of claim 3, wherein the aryl is benzyl.

6. The improvement of claim 1, wherein the alkyl halide contains from 1 to 4 carbon atoms.

7. The improvement of claim 6, wherein the alkyl halide is an alkyl chloride.

8. The improvement of claim 6, wherein the alkyl halide is methyl halide.

9. The improvement of claim 1, wherein the triglyceride diluent is selected from the group consisting of palm oil, palm kernel oil, coconut oil, soybean oil, cottonseed oil, corn oil, canola oil, olive oil, peanut oil, sesame seed oil, linseed oil, safflower seed oil, and mixtures thereof.

10. The improvement of claim 9, wherein the triglyceride diluent is saturated.

11. The improvement of claim 9, wherein the diluent is soybean oil.

12. The improvement of claim 11, wherein the soybean is degummed, refined, bleached soybean oil.

13. The improvement of claim 11, wherein the soybean oil is hydrogenated.

14. The improvement of claim 1, further comprising heating said mixture to a temperature of from 100° to 240° F.

15. The improvement of claim 1, wherein the reaction mixture additionally contains an antifoaming agent.

16. The improvement of claim 15, wherein the antifoaming agent is a silicone antifoaming agent.

17. The improvement of claim 15, wherein the antifoaming agent is dimethyl polysiloxane.

18. The improvement of claim 1, wherein the reaction to produce the quaternary ammonium halide is carried out for from 4 to 24 hours.

19. In a process for the preparation of a quaternary ammonium composition which comprises preparing a mixture consisting essentially of an amine, a diluent, and an alkyl halide alkylating agent to produce said quaternary ammonium composition, the improvement comprising the diluent being selected from the group consisting of fatty acid triglycerides and 2-ethylhexanol.

20. The process of claim 19, wherein the alkyl groups comprising the triglyceride have from about 10 to about 24 carbon atoms.

21. The process of claim 19, wherein the amine is a tertiary amine having the formula

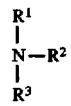

wherein $R^1$ is lower alkyl; $R^2$ is lower alkyl, long-chain alkyl, or aryl; and $R^3$ is long-chain alkyl.

22. The process of claim 21, wherein the lower alkyl contains from 1 to 4 carbon atoms, the long-chain alkyl contains from 10 to 24 carbon atoms, and the aryl is mononuclear.

23. The process of claim 21, wherein the aryl is benzyl.

24. The process of claim 19, wherein the alkyl halide contains from 1 to 4 carbon atoms.

25. The process of claim 24, wherein the alkyl halide is an alkyl chloride.

26. The process of claim 24, wherein the alkyl halide is methyl halide.

27. The process of claim 19, wherein the triglyceride diluent is selected from the group consisting of palm oil, palm kernel oil, coconut oil, soybean oil, cottonseed oil, corn oil, canola oil, olive oil, peanut oil, sesame seed oil, linseed oil, safflower seed oil, and mixtures thereof.

28. The process of claim 27, wherein the triglyceride diluent is saturated.

29. The process of claim 27, wherein the diluent is soybean oil.

30. The process of claim 29, wherein the soybean is degummed, refined, bleached soybean oil.

31. The process of claim 29, wherein the soybean oil is hydrogenated.

32. The process of claim 19, further comprising heating said mixture to a temperature of from 100° to 240° F.

33. The process of claim 19, wherein the reaction mixture additionally contains an antifoaming agent.

34. The process of claim 33, wherein the reaction mixture additionally contains a silicone antifoaming agent.

35. The process of claim 33, wherein the antifoaming agent is dimethyl polysiloxane.

36. The process of claim 19, wherein the reaction to produce the quaternary ammonium halide is carried out for from 4 to 24 hours.

37. The improvement of claim 1, further comprising heating said mixture to a temperature of from 50° to 220° F.

38. The process of claim 19, further comprising heating said mixture to a temperature of from 50° to 220° F.

39. The improvement of claim 1, wherein the diluent is 2-ethylhexanol.

40. The process of claim 19, wherein the diluent is 2-ethylhexanol.

* * * * *